United States Patent [19]

Lang et al.

[11] Patent Number: 4,777,039
[45] Date of Patent: Oct. 11, 1988

[54] PEARLESCENT HAIR CONDITIONING COMPOSITION

[75] Inventors: Günther Lang, Reinheim; Paul Gross, Darmstadt; Friedel Schröder, Darmstadt; Karin Grundmann, Darmstadt, all of Fed. Rep. of Germany

[73] Assignee: Wella Aktiengesellschaft, Darmstadt, Fed. Rep. of Germany

[21] Appl. No.: 878,870

[22] PCT Filed: Oct. 31, 1985

[86] PCT No.: PCT/EP85/00579
§ 371 Date: Jun. 13, 1986
§ 102(e) Date: Jun. 13, 1986

[87] PCT Pub. No.: WO86/02828
PCT Pub. Date: May 22, 1986

[30] Foreign Application Priority Data

Nov. 9, 1984 [DE] Fed. Rep. of Germany ....... 3440935

[51] Int. Cl.$^4$ ........................ A61K 7/075; A61K 7/08
[52] U.S. Cl. ........................................................ 424/70
[58] Field of Search ........................................ 424/70

[56] References Cited

U.S. PATENT DOCUMENTS

| 4,007,261 | 2/1977 | Sorrentino et al. | 424/70 |
| 4,275,055 | 6/1981 | Nachtigal et al. | 424/70 |
| 4,333,921 | 6/1982 | Luedicke et al. | 424/70 |
| 4,438,096 | 3/1984 | Preston | 424/70 |

FOREIGN PATENT DOCUMENTS 3506543 8/1986 Fed. Rep. of Germany.

*Primary Examiner*—John E. Kittle
*Assistant Examiner*—Susan S. Rucker
*Attorney, Agent, or Firm*—Michael J. Striker

[57] ABSTRACT

Pearlescent hair conditioning composition based on a quaternary compound and a fatty alcohol, consisting of (A) 0.2 to 10 percent by weight coconut fatty acid monoethanolamide, (B) 0.4 to 10 percent by weight of a straight-chain fatty alcohol with m carbon atoms (m=14 to 18), (C) 0.1 to 4 percent by weight of a quaternary compound of the formula

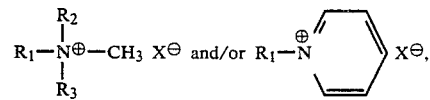

wherein $R_1=C_n$-alkyl (n=12–22), coconut amidoethyl, coconut amidopropyl, R′—Y (R′—$C_n$-alkyl, Y=—O—C(O)—CH$_2$- or —C(O)—O—CH$_2$CH$_2$—) $R_2$=CH$_3$, CH$_2$CH$_2$OH or CH$_2$CH$_3$, $R_3$=CH$_3$, CH$_2$CH$_2$OH, benzyl or acetamidyl, X$^\ominus$=Cl$^-$, Br$^-$, CH$_3$SO$_4^-$, ½SO$_4^{2-}$, lactate$^-$ or acetate$^-$, (D) 70 to 99.3 percent by weight water and (E) 0 to 24 percent by weight conventional cosmetic added substances, wherein m+n≧29, A/B is 0.1 to 3, C/A+B=0.05 to 0.5, and the proportion by weight of the added substances is not greater than the sum of A+B+C.

13 Claims, No Drawings

PEARLESCENT HAIR CONDITIONING COMPOSITION

Damage to the hair structure is brought about through frequent bleaching, permanent waving, and dyeing, but also by means of frequent washing of the hair with fat-removing tensides, as well as by means of the intensive action of sunlight. The hair becomes brittle and loses its luster. In addition, the hair is charged electrostatically during combing, and the roughened hair surface causes matting and knotting of the hair. Combing is made very difficult by means of this. Hair conditioning compositions which act so as to improve combing facility and which have a caring effect have therefore achieved considerable importance. In particular, through the use of hair conditioning compositions, such as hair treatments and rinses, the combing facility of hair is improved, and the electrostatic charging during combing is prevented. The hair conditioning compositions are chiefly in the form of oil-in-water emulsions, for example, as so-called cream rinses, and contain semisolid or solid substances, such as paraffin oil, petrolatuem, wool fat, wool fat alcohols, fatty acid esters, and hydrocarbon waxes, as framework component parts. Quaternary ammonium compounds such as oxyethylated alkylammonium phosphates, alkyltrimethylammoniumchlorides, dialkyldimethylammoniumchlorides, alkyldimethylbenzylammoniumchlorides, and alkylpyridiniumchlorides, are normally used alone or in combination with nonionogenic emulsifiers as emulsifiers for such emulsions.

The recipes most often used contain quaternary ammonium salts and fatty alcohols, in particular. These compositions have a milky-cloudy appearance. Although, in the past, there has been no lack of attempts to impart a pearlescent, more aesthetic appearance to such products, there has been no success previously in making available such a product with authentic pearlescence. While pearlescent recipes are state of the art in the area of shampoos and are often used, it is obviously problematic to produce pearlescent, stable, cationic compositions containing fatty alcohols. Thus, for example, a pearlescent, cationic hair treatment is described in U.S. Pat. No. 4,275,055 which, however, contains a high proportion of stearyldimethylbenzylammoniumchloride, which has a high melting point and is difficult to dissolve, and no fatty alcohol. Other hair conditioning compositions with pearlescence are not purely cationic, but, rather, contain high proportions of anionic and nonionic tensides. Moreover, such known pearlescent hair conditioning compositions with satisfactory characteristics contain relatively expensive raw materials.

Therefore, it was the object of the present invention to provide pearlescent hair conditioning compositions with good use characteristics based on the relatively low-priced raw materials fatty alcohol and quaternary compound.

It was found, in addition, that this object is met by means of pearlescent hair conditioning composition based on a quaternary compound and a fatty alcohol consisting of (A) 0.2 to 10 percent by weight coconut fatty acid monoethanolamide, (B) 0.4 to 10 percent by weight of a straight-chain fatty alcohol with m carbon atoms, wherein m is a number from 14 to 18, or a mixture of such fatty alcohols, wherein m then indicates the average quantity of carbon atoms, (C) 0.1 to 4 percent by weight of a quaternary compound of the general formula

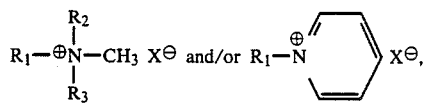

wherein $R_1$ designates an alkyl radical with n carbon atoms (n=12 to 22), coconut amidoethyl, coconut amidopropyl, $R'$—Y— with $R'=C_{12}$ to $C_{20}$-alkyl and

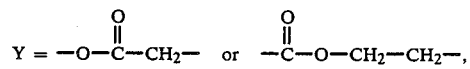

$R_2$ is one of the radicals $CH_3$, $CH_2CH_2OH$ or $CH_2CH_3$, $R_3$ designates $CH_3$, $CH_2CH_2OH$, benzyl or acetamidyl and $X^\ominus = Cl^-$, $Br^-$, $CH_3SO_4^-$, $\frac{1}{2}SO_4^{2-}$, lactate$^-$ or acetate$^{-1}$, (D) 70 to 99.3 percent by weight water and (E) 0 to 24 percent by weight of other cosmetic added substances, wherein the sum formed from the number of carbon atoms of the fatty alcohol (m) and the number of carbon atoms of the radical $R_1$ of the quaternary compound (n) is greater than or equal to 29 (m+n≧29), assuming that the weight ratio of the component A to the component B is between 0.1 and 3 and the weight ratio of the component C to the sum of components A and B is between 0.05 and 0.5, and assuming that the proportion by weight of the cosmetic added substances is not greater than the proportion by weight from the sum of components A, B, and C.

The hair conditioning compositions, according to the invention, have an effect which very favorably improves combing facility, a uniform viscosity and a stable, pearlescent appearance.

It is particularly advantageous if the component A (coconut fatty acid monoethanolamide) is contained in a quantity of 0.5 to 4 percent by weight in the compositions.

The particularly preferred insertion quantity for component B (fatty alcohol) is 0.8 to 5 percent by weight. All straight-chain fatty alcohols with 14 to 18 carbon atoms, e.g. tetradecanol, cetyl alcohol, and stearyl alcohol, come under consideration as fatty alcohols. Moreover, component B can consist of a fatty alcohol mixture, for example, of a 50:50 mixture of cetyl alcohol and stearyl alcohol (commercial product LANETTE O of the firm Henkel, Düsseldorf); the average number of carbon atoms of fatty alcohol component B is then m=17.

Hair conditioning compositions with particularly handsom and intensive pearlescence are obtained when component B consists of cetyl alcohol or stearyl alcohol or of a mixture of the two alcohols, and component C consists of cetyltrimethylammoniumchloride or stearyltrimethylammoniumchloride or a mixture of these two cationic compounds. Moreover, these hair conditioning compositions have the advantage that they have a stable pearlescence also at temperatures of over 40° C.

A particularly preferred embodiment form of the hair conditioning composition described is, then, provided, in addition, when the weight ratio of component A to component B is 0.3 to 2.

Primarily, quaternary ammonium compounds, such as lauryltrimethylammoniumchloride, tetradecyltrimethylammoniumchloride, cetyltrimethylammoniumchloride, stearyltrimethylammoniumchloride, cetyldimethylhydroxyethylammoniumdihydrogenphosphate, cetyldimethylbenzylammoniumchloride, and pyridinium salts, such as cetylpyridiniumchloride, and other quaternary compounds, in addition, such as lauryl acid cholinesterchloride, betaine cetylesterchloride, and coconut fatty acid amidopropyldimethylacetamidylammoniumchloride, are contained as suitable quaternary compounds of component C, preferably in a quantity of 0.1 to 1.5 percent by weight.

The main quantity of the composition, according to the invention, consists of water, wherein the water content is preferably 90 to 97 percent by weight. Although tap water can be used if it contains a relatively low proportion of ions, it is preferable to use deionized water.

In addition, the hair conditioning compositions described here can contain all those cosmetic added substances that are conventionally used in hair conditioning compositions, particularly dyestuffs, perfume oil, vitamins, preservatives, and antioxidants, as well as active ingredients against dandruff. The aforementioned added substances can be contained, in each instance, in quantities up to 1 percent by weight. Other conventional added substances are, e.g. cosmetically active oils such as, e.g. avocado oil, or maintaining substances such as, e.g. lanoline, cholesterol, and pantothenic acid, wherein these added substances can be contained in a quantity of up to 10 percent by weight. In addition, the compositions can have, as added substances, cationic resins, as well as thickeners, e.g. starch, cellulose derivatives or highly dispersed silicic acid (e.g. Aerosil ®300 of the firm Degussa, Hanau, Federal Republic of Germany) in a quantity of up to 2 percent by weight.

The hair conditioning compositions, according to the invention, are also available in the form of aerosol preparations and then contain up to 10 percent by weight propellant as an additional added substance. Chlorfluoralkanes such as, e.g. $CCl_3F$, $CCl_2F_2$, $C_2Cl_3F_3$, $CCl_2FCCl_2F$, $CHCl_2F$, $CHClF_2$, and $CClF_2-CClF_2$, readily volatile hydrocarbons such as, e.g. n-butane and n-propane, or, also, dimethylether, $CO_2$, $N_2O$, $N_2$, $CH_2Cl_2$ and $CCl_3-CH_3$, can be used as propellant.

The production of the compositions, according to the invention, is effected according to the conventional production processes for cosmetic emulsions in that, for example, the hydrophobic components (components A and B, as well as hydrophobic added substances which may possibly be contained) are first melted at 90° C., and then the hydrophilic components (component C, as well as hydrophobic added substances) are dissolved in water. Next, the aqueous solution is heated to 90° C. and emulsified into the melting of hydrophobic component parts accompanied by stirring. Finally, the occurring emulsion is cooled.

The following examples will explain the subject matter of the invention in more detail.

EXAMPLES 1 to 20

In order to obtain the occurrence of pearlescence in the compositions in dependence on the length of the alkyl chain of the fatty alcohol used and of the alkyl radical in the quaternary compound, fatty alcohols with alkyl chain lengths of $C_{12}$ to $C_{18}$ were combined with alkyltrimethylammonium salts of the chain lengths $C_{12}$ to $C_{18}$ in a hair conditioning composition, according to the invention, having the following composition:

| | |
|---|---|
| (A) | 1.35 percent by weight coconut fatty acid monoethanolamide |
| (B) | 2.00 percent by weight fatty alcohol |
| (C) | 0.55 percent by weight quaternary compound |
| | 0.30 percent by weight perfume oil |
| | 0.10 percent by weight dyestuff |
| | 95.70 percent by weight water, de-ionized |
| | 100.00 percent by weight. |

The results of the test are presented in the following in the form of Table 1. As can be seen from Table 1, the aforementioned composition produces pearlescence only for those combinations of fatty alcohol and quaternary compound in which the sum of the carbon atoms of the alkyl radical of the fatty alcohol and the quaternary compound is greater than or equal to 29 (Examples 4, 5, 8–10, 12–15 and 17–20).

TABLE 1

Occurrence of pearlescence in dependence on the alkyl chain length of the fatty alcohol ($C_m$) and of the alkyl radical of the quarternary compound ($C_n$).

| quaternary compound ($C_n$) | Fatty alcohol ($C_m$) | | | | |
|---|---|---|---|---|---|
| | $C_{12}$ Dodecyl alcohol | $C_{14}$ Tetradecyl alcohol | $C_{16}$ Cetyl alcohol | $C_{16/18}$ Cetyl-stearyl alcohol | $C_{18}$ Stearyl alcohol |
| $C_{12}$ Lauryltrimethyl-ammonium-chloride | 1 — | 2 — | 3 — | 4 + | 5 + |
| $C_{14}$ Tetradecyl-trimethyl-ammoniumchloride | 6 — | 7 — | 8 + | 9 + | 10 + |
| $C_{16}$ Cetyltrimethyl-ammoniumchloride | 11 — | 12 + | 13 + | 14 + | 15 + |
| $C_{18}$ Stearyltrimethyl-ammoniumchloride | 16 — | 17 + | 18 + | 19 + | 20 + |

+ = pearlescence
− = no pearlescence
Bold border = compositions according to the invention ($C_m + C_n \geq 29$)

EXAMPLES 21 to 25

Hair Conditioning Composition

Examples 21–25 show the usability of additional cationic compounds. In each instance, 20 g of the following hair conditioning composition are distributed in the washed hair and rinsed out with water after an acting time of 3 to 5 minutes. The hair has obtained a good combing facility and an excellent hold. The hair conditioning compositions also have a stable pearlescence after more prolonged storage. (Data in percent by weight).

|   |   | Example No. | | | | |
|---|---|---|---|---|---|---|
|   |   | 21 | 22 | 23 | 24 | 25 |
| (A) | Coconut fatty acid monoethanolamide | 1.36 | 1.76 | 1.76 | 1.76 | 1.76 |
| (B) | Stearyl alcohol | 1.90 | 1.90 | 1.90 | 1.90 | 1.90 |
| (C) | Cetyldimethylbenzylammoniumchloride | 0.54 | — | — | — | — |
|   | Cetylpyridiniumchloride | — | 0.53 | — | — | — |
|   | $C_{20-22}$—alkyltrimethyylammoniumchloride | — | — | 0.66 | — | — |
|   | Cetyldimethylhydroxyethylammoniumdihydrogenophosphate | — | — | — | 0.54 | — |
|   | Coconut fatty acid amidopropyldimethyl-acetamidylammoniumchloride | — | — | — | — | 1.27 |
|   | Perfume oil | 0.30 | 0.30 | 0.30 | 0.30 | 0.70 |
|   | Dyestuff | 0.10 | 0.10 | 0.10 | 0.10 | 0.10 |
|   | Water | 95.80 | 95.41 | 95.28 | 95.40 | 94.27 |
|   |   | 100.00 | 100.00 | 100.00 | 100.00 | 100.00 |
|   | A/B | 0.70 | 0.92 | 0.92 | 0.92 | 0.92 |
|   | $\frac{C}{A+B}$ | 0.16 | 0.15 | 0.22 | 0.15 | 0.34 |

EXAMPLES 26 to 30

Hair Conditioning Composition (Data in percent by weight)

|   |   | Example No. | | | | |
|---|---|---|---|---|---|---|
|   |   | 26 | 27 | 28 | 29 | 30 |
| (A) | Coconut fatty acid mono-ethanolamide | 0.76 | 1.19 | 1.27 | 1.46 | 2.20 |
| (B) | Stearyl alcohol | 2.54 | 2.39 | 1.81 | 1.69 | 1.10 |
| (C) | Stearyltrimethylammonium-chloride | 0.65 | 0.40 | 0.86 | 0.73 | 0.65 |
|   | Perfume oil | 0.20 | 0.20 | 0.20 | 0.20 | 0.20 |
|   | Water | 95.85 | 95.82 | 95.86 | 95.92 | 95.85 |
|   |   | 100.00 | 100.00 | 100.00 | 100.00 | 100.00 |
|   | A/B | 0.30 | 0.50 | 0.70 | 0.86 | 2.00 |
|   | $\frac{C}{A+B}$ | 0.19 | 0.11 | 0.28 | 0.27 | 0.19 |

EXAMPLES 31 and 32

Medium-Viscous Hair Conditioning Composition

The following examples 31 and 32 show stable, pearlescent hair conditioning compositions of medium viscosity with good characteristics in terms of application technology. They show the usability of cationic tensides, which are easily degradable and therefore load the environment to a particularly low degree, as quaternary compound for the composition, according to the invention. (Data in percent by weight).

|   |   | Example No. | |
|---|---|---|---|
|   |   | 31 | 32 |
| (A) | Coconut fatty acid monoethanolamide | 1.76 | 1.76 |
| (B) | Cetylstearyl alcohol | 1.96 | 1.96 |
| (C) | Betainecetylester chloride | 0.60 | — |
|   | Lauryl acid cholinesterchloride | — | 0.60 |
|   | Perfume oil | 0.50 | 0.50 |
|   | Dyestuff | 0.10 | 0.10 |
|   | Water | 95.08 | 95.08 |
|   |   | 100.00 | 100.00 |
|   | A/B | 0.90 | 0.90 |
|   | $\frac{C}{A+B}$ | 0.16 | 0.16 |

EXAMPLE 33

Highly Viscous Hair Conditioning Composition

The hair conditioning composition, listed as follows, is a highly viscous, pearlescent hair treatment which is applied as described for examples 21 to 25. Damaged hair shows a good combing facility, as well as greater fullness (body effect) after application.

| (A) | Coconut fatty acid mono-ethanolamide | 3.10 percent by weight |
|---|---|---|
| (B) | Cetylstearyl alcohol | 4.42 percent by weight |
| (C) | Cetyltrimethylammoniumchloride | 1.24 percent by weight |
|   | highly dispersed silicic acid (Aerosil ® 300) | 0.50 percent by weight |
|   | Perfume oil | 0.50 percent by weight |
|   | Water | 90.24 percent by weight |
|   |   | 100.00 percent by weight |

A/B = 0.7

$\frac{C}{A+B} = 0.16$

EXAMPLE 34

Aerosol Foam Treatment

A handsome pearlescence is to be observed in the composition, listed as follows, in case it is provided in a transparent aerosol container. The aerosol container is shaken before the product is discharged. The composition exits in the form of a creamy foam with very good conditioning action. The application of the composition is effected in the manner described in examples 21 to 25.

| (A) | Coconut fatty acid monoethanolamide | 0.62 percent by weight |
|---|---|---|
| (B) | Cetylstearyl alcohol | 0.88 percent by weight |
| (C) | Cetyltrimethylammonium-chloride | 0.13 percent by weight |
|   | Dyestuff | 0.30 percent by weight |
|   | Perfume oil | 0.20 percent by weight |
|   | Water | 97.87 percent by weight |
|   |   | 100.00 percent by weight |

92 percent by weight of the above composition are provided, together with 8 percent by weight of a propellant mixture consisting of 50 percent by weight propane and 50 percent by weight butane, in a transparent aerosol container.

We claim:

1. Pearlescent hair conditioning composition based on a quaternary compound and a fatty alcohol, consisting of
(A) 0.2 to 10% by weight coconut fatty acid monoethanolamide
(B) 0.4 to 10% by weight of a straight-chain fatty alcohol with m carbon atoms, wherein m is a number from 14 to 18, or of a mixture of such fatty alcohols, wherein m then designates the average number of carbon atoms,
(C) 0.1 to 4% by weight of a quaternary compound of the general formula $$R_1-\overset{R_2}{\underset{R_3}{\overset{|}{N^{\oplus}}}}-CH_3 \; X^{\ominus} \text{ and/or } R_1-\overset{\oplus}{N}\diagdown\!\!\diagup X^{\ominus},$$

wherein
$R_1$ designates an alkyl radical with n carbon atoms (n=12 to 22), coconut amidoethyl, coconut amidopropyl, R'—Y— with R'=$C_{12}$ to $C_{20}$—alkyl and $$Y = -O-\overset{O}{\underset{}{\overset{\|}{C}}}-CH_2- \text{ or } -\overset{O}{\underset{}{\overset{\|}{C}}}-O-CH_2-CH_2-,$$

$R_2$ is one of the radicals $CH_3$, $CH_2CH_2OH$ or $CH_2CH_3$,
$R_3$ designates $CH_3$, $CH_2CH_2OH$, benzyl or acetamidyl, and
$X^{\ominus}$ = $Cl^-$, $Br^-$, $CH_3SO_4^-$, $\frac{1}{2}SO_4^{2-}$, lactate$^-$ or acetate$^-$,
(D) 70 to 99.3 % by weight water and
(E) 0 to 24 % by weight conventional cosmetic added substances,
wherein the sum formed from the number of carbon atoms of the fatty alcohol (m) and the number of carbon atoms of the radical $R_1$ of the quaternary compound (n) is greater than or equal to 29 (m+n≧29), assuming that the weight ratio of component A to component B is between 0.1 and 3, and the weight ratio of component C to the sum of said components A and B is between 0.05 and 0.5, as well as assuming, in addition, that the proportion by weight of said cosmetic added substances is not greater than the proportion by weight of the sum of said components A, B and C.

2. Composition according to claim 1, characterized in that said component A is contained in a quantity of 0.5 to 4 percent by weight.

3. Composition according to claim 1, characterized in that said component B is contained in a quantity of 0.8 to 5 percent by weight.

4. Composition according to claim 1, characterized in that said component C is contained in a quantity of 0.1 to 1.5 percent by weight.

5. Composition according to claim 1, characterized in that it contains 90 to 97 percent by weight water.

6. Composition according to claim 1, characterized in that said component B consists of cetyl alcohol and/or stearyl alcohol, and said component C consists of cetyltrimethylammoniumchloride and/or stearyltrimethylammoniumchloride.

7. Composition according to claim 1, characterized in that the weight ratio of said component A to said component B is 0.3 to 2.

8. Composition according to claim 1, characterized in that said quaternary compound is selected from lauryltrimethylammoniumchloride, tetradecyltrimmethylammoniumchloride, cetyltrimethylammoniumchloride, stearyltrimethylammoniumchloride, cetyldimethylbenzylammoniumchloride, cetylpyridiniumchloride, cetyldimethylhydroxyethylammoniumdihydrogenphosphate, lauryl acid cholinesterchloride, betainecetylesterchloride, and coconut fatty acid amidopropyldimethylacetamidylammoniumchloride.

9. Composition according to claim 2, characterized in that said component B is contained in a quantity of 0.8 to 5 percent by weight.

10. Composition according to claim 3, characterized in that said component C is contained in a quantity of 0.1 to 1.5 percent by weight.

11. Composition according to claim 2, characterized in that it contains 90 to 97 percent by weight water.

12. Composition according to claim 3, characterized in that said component B consists of cetyl alcohol and/or stearyl alcohol, and said component C consists of cetyltrimethylammoniumchloride and/or stearyltrimethylammoniumchloride.

13. Composition according to claim 2, characterized in that the weight ratio of said component A to said component B is 0.3 to 2.

* * * * *